United States Patent [19]

Kownacki et al.

[11] Patent Number: 5,302,125
[45] Date of Patent: Apr. 12, 1994

[54] DENTAL PROSTHETIC IMPLANT

[76] Inventors: Charles D. Kownacki, 2714 W. 23rd St., Erie, Pa. 16506; Wade W. Prescott, 3011 Deeb Ct., Vista, Calif. 92084

[21] Appl. No.: 964,747

[22] Filed: Oct. 22, 1992

[51] Int. Cl.⁵ .................... A61C 13/12; A61C 13/225; A61C 8/00
[52] U.S. Cl. ..................................... 433/172; 433/173
[58] Field of Search ............... 433/173, 174, 175, 176, 433/172

[56] References Cited

U.S. PATENT DOCUMENTS

| 4,568,285 | 2/1986 | Chiaramonte et al. | 433/173 |
|---|---|---|---|
| 4,793,808 | 12/1988 | Kirsch | 433/173 |
| 4,832,601 | 5/1989 | Linden | 433/173 |
| 4,854,874 | 8/1989 | Neuwirth | 433/172 |
| 4,907,969 | 3/1990 | Ward | 433/173 |
| 4,960,381 | 10/1990 | Niznick | 433/173 |
| 5,030,096 | 7/1991 | Hurson et al. | 433/173 |
| 5,073,111 | 12/1991 | Daftary | 433/173 |

FOREIGN PATENT DOCUMENTS 2663836  1/1992  France ................. 433/175

Primary Examiner—Gene Mancene
Assistant Examiner—Nicholas D. Lucchesi
Attorney, Agent, or Firm—Richard K. Thomson

[57] ABSTRACT

A dental prosthetic implant which has angular rotational capability and improved locking between the implant fixture and the abutment prosthesis. The rotation and locking system includes an implant fixture with an internal spherical radius at its upper portion. A top seat with the same spherical radius is secured to the top portion of the fixture. A locking element configured as a sphere with flexible locking fingers on its lower portion and an internal cylindrical bore through its center that has a conically tapered lower portion is received between the implant fixture and the main body of the abutment. The conically tapered lower portion may taper inwardly or outwardly and is engaged by a similarly configured portion of the flexible fingers. A threaded portion of the locking screw engages in a threaded bore in the implant providing the force to bias the flexible fingers outwardly into firm engagement with a complementarily configured surface on the fixture, as well as increasing the pressure between the upper surface of the locking element and the nether surface of the top seat.

18 Claims, 7 Drawing Sheets

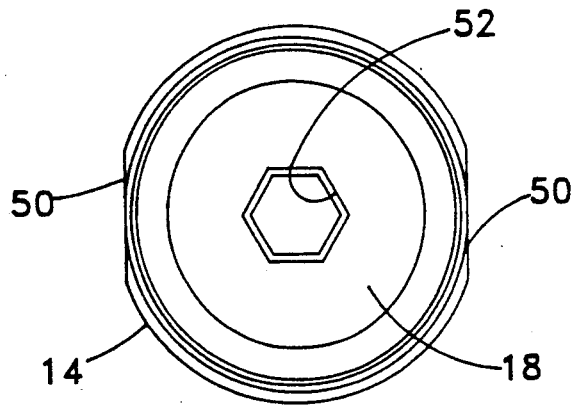
Fig. 1a
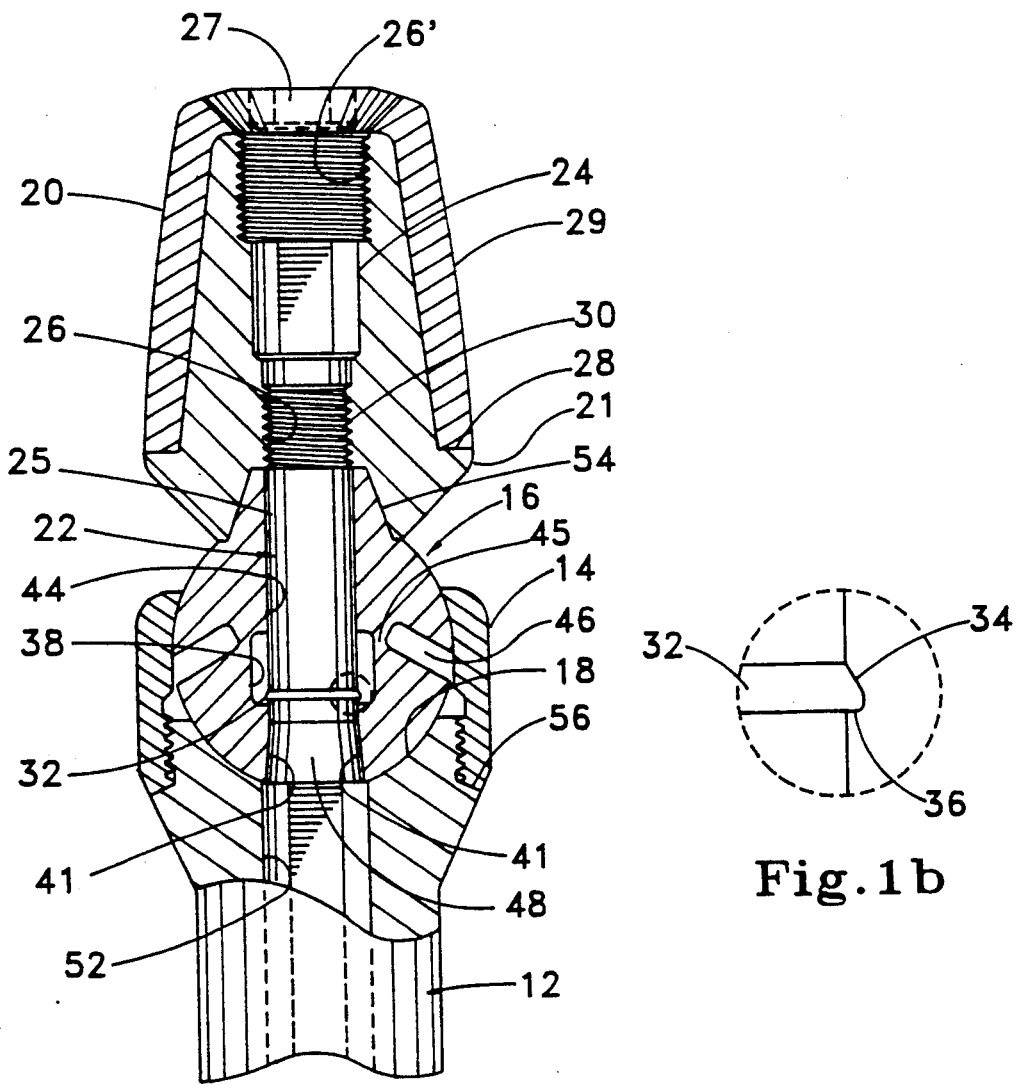
Fig. 1
Fig. 1b

DENTAL PROSTHETIC IMPLANT

BACKGROUND AND SUMMARY OF THE INVENTION

This invention relates to the field of dental prosthetic implants. More particularly, this invention is directed to an improved dental prosthetic implant with enhanced angular rotation and locking capabilities once the abutment has been positioned in a preferred position relative to the implant fixture.

The field of dental prosthetic devices is a rapidly growing industry with dental implants beginning to garner an increased market share as opposed to the old-fashioned removable dentures, partial dentures or conventional bridges. A large number of implant systems have been developed by individuals wanting to sink their teeth into this expanding piece of pie.

These systems are typically comprised of two principal components: an implant fixture that is imbedded into the jaw bone (maxilla or mandible) of the patient, and an abutment which typically forms a support for the prosthesis, i.e., a crown, a denture, partial or bridge abutment. The implant fixture will be surgically implanted at an angle that will vary based on a plurality of factors: the number of implants being placed into the corresponding section of bone that is edentulous, that portion of the edentulous area that has the most bone support to place the implant with the greatest success, and the angle chosen by the professional that is placing the implant. The abutment, on the otherhand, needs to be positioned relative to its opposing tooth so that proper occlusion may result for good function.

In some systems, a myriad of shims of varying angularity are used between the implant fixture and the abutment to provide the desired relative positioning for these two elements to ensure proper occlusion. Such an implant system is complicated by literally hundreds of different pieces which must be properly selected and assembled. There are other systems that use pre-fabricated angled abutments, but these systems have problems relative to their rotational locations.

More recently, the abutment has been attached to the implant fixture by a ball-and-socket joint and a set screw has been used to lock the two elements into the desired angular and rotational position. The problem with these systems is that the force exerted by the muscles of mastication can exceed 250 lbs/sq.in. which, when applied near the edge of a biting or chewing surface, can produce torsional forces capable of overpowering the retention force created by the relatively small frictional surface area of the set screw, thereby displacing the prosthetic tooth.

Therefore, the present invention provides a dental prosthetic implant with an enhanced rotational and locking capability. It further provides an implant that is designed for proper hygene significantly reducing the potential for micro-leakage. Lastly, the implant of this invention provides a system which has been designed to use significantly fewer pieces than prominent previous systems.

These features are provided by a dental implant fixture and positionable abutment. The abutment has a plurality of flexible fingers which can be expanded by virtue of a locking screw into engagement with a portion of the implant fixture to secure the abutment in a particular rotational and/or pivotal position. The portion of the abutment containing the flexible fingers may be formed integrally on a separate element which is secured to the main body by virtue of a retaining protrusion on the locking screw or formed integrally with the main body of the abutment.

In one embodiment, a retaining ring is formed on the locking screw to secure it to a separable ball element of the abutment. The actuating portion of the flexible fingers and associated portion of the locking screw may be tapered outwardly so the locking screw acts in tension and provides an upwardly and outwardly directed force or, alternatively, these portions may be tapered inwardly so that the locking screw acts in compression so the locking screw provides a downwardly and outwardly directed force. In either case, the flexible fingers interact with a complementary surface on the implant fixture to secure the abutment against undesired rotational and/or pivotal movement.

Various other features advantages and characteristics of the present invention will become apparent after a reading of the following detailed description of the preferred embodiments.

BRIEF DESCRIPTION OF THE DRAWINGS

The Figures depict the preferred embodiments of the present invention, like parts bearing like reference numerals, in which:

FIG. 1 is a cross-sectional side view of a first embodiment of the dental implant fixture with separate adjustable abutment;

FIG. 1A is a top view of the implant fixture with the top seat in place and the abutment removed;

FIG. 1B is an enlargement of the portion of the locking screw circled in FIG. 1;

DETAILED DESCRIPTION OF THE PREFERRED EMBODIMENTS

Figures 2, 2A:
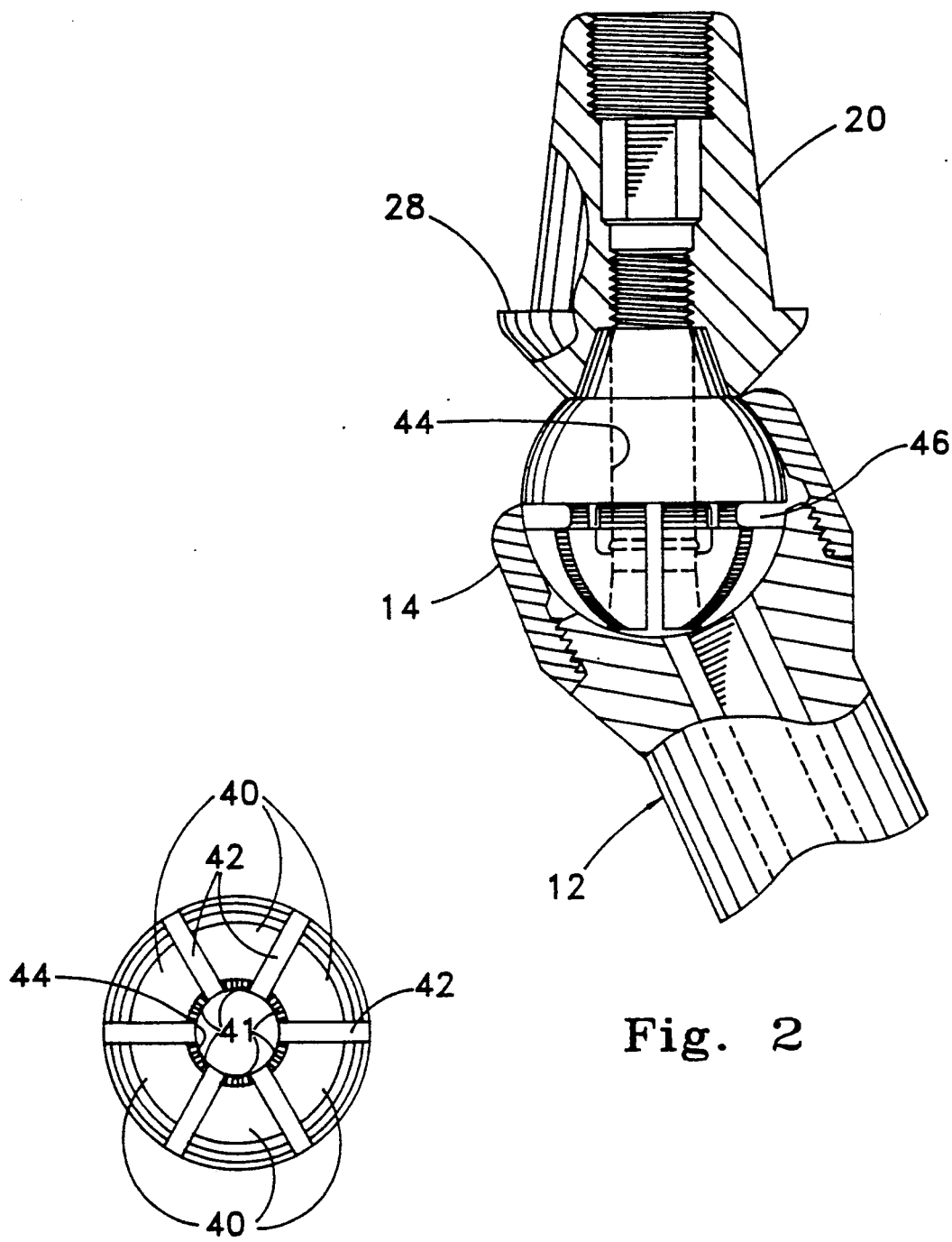
FIG. 2 is a cross-sectional side view of the embodiment shown in FIG. 1 showing the maximum angular tilt of the abutment.
FIG. 2A is a bottom view of the abutment depicted in FIG. 2.

A first embodiment of the dental prosthetic implant device of the present invention is shown in FIG. 1, generally at 10. Device 10 is comprised of two principal elements: an implant fixture 12 and an abutment 20. The external surface of fixture 12 is normally equipped with threads which will anchor the fixture 12 in the patient's maxilla or mandible, 15 (see FIG. 7). Since the thread configuration forms no part of the present invention, that detail is omitted for the sake of clarity. A top seat 14 of fixture 12 captures and helps retain rotational locking element 16. In this embodiment, locking element 16 is formed as a separate sphere that is attached to a main portion 21 of abutment 20 by means of locking screw 22.

Internal hex 24 in the main body 21 permits rotational and angular adjustment of main body 21 by virtue of internal threads 26 which engage complementary threads 30 on locking screw 22. Smooth cylindrical portion 25 of screw 22 permits relative sliding movement between locking screw 22 and locking element 16. The external surface of abutment 20 is tapered and has a protruding base 28 for receiving a casting sleeve 29 upon which a dental casting may be made, the casting providing the internal dimensions of the prosthetic tooth. Internal threads 26' are provided for attachment of a securing screw 27 which is used to attach a bar connector 72 (FIG. 7) when the installation of the fixture 12 and abutment 20 has been completed.

An annular protrusion 32 is formed near one end of smooth cylidrical protion 25. Protrusion 32 serves to secure locking screw 22 to locking element 16. As more clearly seen in FIG. 1B, protrusion has a ramping taper 34 on an upper face and a horizontal surface 36 on its lower face. Flexible fingers 40 (FIG. 2a) can be pushed outwardly by ramping taper 34 and snap in behind protrusion 32 engaging horizontal surface 36. A hollowed out area 38 in locking element 16 receives protrusion 32.

Fingers 40 are formed by a plurality of diametrical slots 42 (FIG. 2), the plane of each such slot containing the longitudinal central axis of axial bore 44 through locking element 16. A circumferential relief groove 46 enhances the flexibility of fingers 40 by making the knuckle portion 45 thinner. By angulating groove 46 upwardly, fingers 40 are made longer, which further adds to their flexibility, while keeping the outer portion of groove 46 low enough that it is not exposed outside top seat 14 during maximum tilting (preferably about 30°) of abutment 20 (FIG. 2). Unlike certain other implant systems, the present invention has no exposed recesses or threads which may produce dental hygene problems including micro-leakage, i.e., bacterial migration into the internal spaces in the implant.

A lower section of locking screw 22 abutting smooth cylindrical portion 25 has a conical taper 48 formed thereon. In this embodiment, conical taper 48 is tapered outwardly and locking screw 22 operates in tension. In use, flats 50 (FIG. 1A) on top seat 14 will be engaged by a small wrench (not shown) to retain it against rotational movement during tightening of abutment 20 using hex socket 24. As internal threads 26 in abutment 20 are advanced on threads 30 of locking screw 22, conical taper 48 engages complementary sloping surfaces on the ends 41 of fingers 40 thereby biasing the outer periphery of flexible fingers 40 outwardly into firm engagement with a complementary (in this case, hemispherical) surface 18. The diametrical slots 42, in essence, dig into the face of surface 18 and prohibit both rotation about the longitudinal axis 44 of abutment 20 and rotation about any axis which is orthogonal to the longitudinal axis (tilting). It is believed that the ends 41 (FIG. 2) of fingers 40 play a significant role in preventing tilting. As flexible fingers 40 are biased outwardly, the top surface of locking element 16 is forced against the nether surface of top seat 14.

An internal hex socket 52 in implant fixture 12, used to seat the fixture in maxilla or mandible 15, preferably can be operated by the same hex driver as socket 24, for the sake of simplicity. Locking element 16 and main body 21 have complementary frustoconical surfaces which form a joint 54. This joint is preferably water tight and may be provided with a seal (not shown), if necessary. A second joint 56 limits how tightly the spherical surfaces on top seat 14 and fixture 12 (surface 18) can engage the unexpanded locking element 16.

Figure 3:
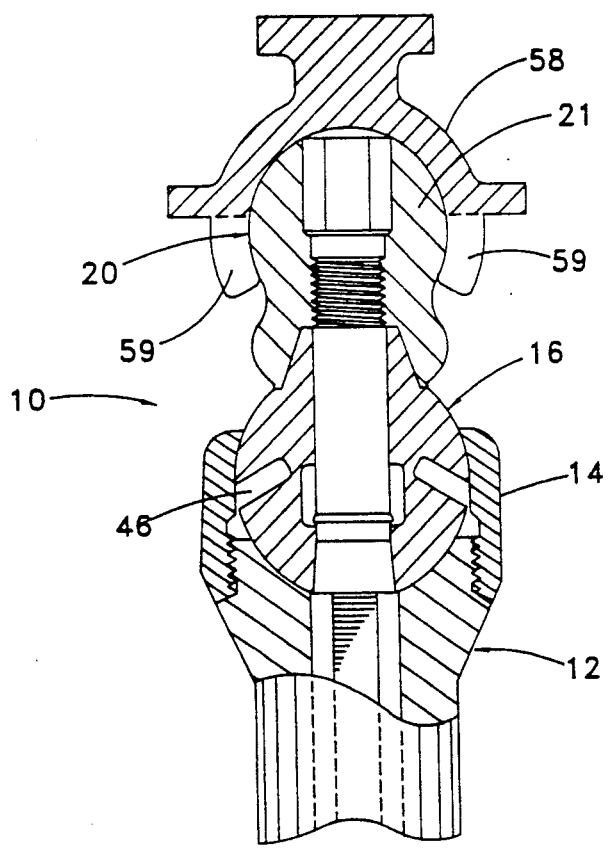
FIG. 3 is a cross-sectional side view of a second embodiment having the main body of the abutment formed as a separate ball.

FIG. 3 depicts a second embodiment of the dental prosthetic implant 10 of the present invention. In this embodiment, the abutment 20 has a spherical, rather than tapered, upper surface and is received in a female socket member 58 upon which a cosmetic dental element can be molded in place. Fingers 59 on socket member 58 engage spherical body 21 and permit some limited pivoting between member 58 and body 21. However, the primary rotational and pivotal adjustment is provided by locking element 16, as in the previous embodiment. Fingers 59 have sufficient flexibility to snap around body 21.

Figure 4:
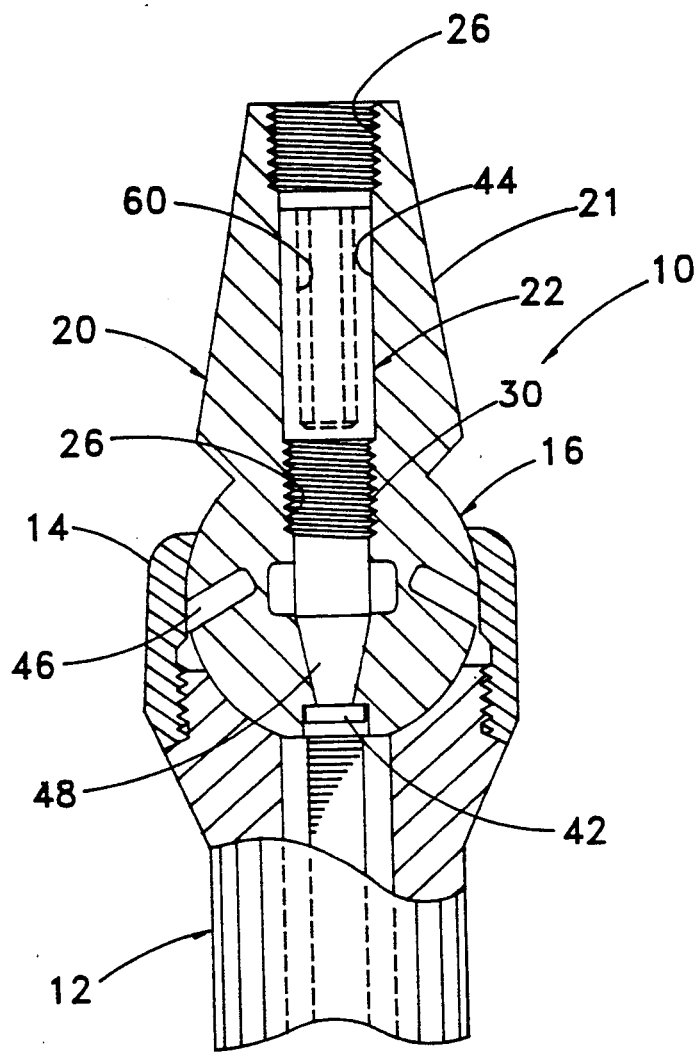
FIG. 4 is a cross-sectional side view of a third embodiment in which the abutment is formed integrally with the locking mechanism.

FIG. 4 depicts a third embodiment of the dental prosthetic implant 10 of the present invention. In this embodiment, locking element 16 is formed integrally with main body 21. The second key difference is that the taper 48 is an inward taper and acts in compression to push flexible fingers outwardly. An annular protrusion 32 is formed on the end of locking screw 22. Hex socket 60 is formed internally within locking screw 22 in order to permit adjustment between external threads 30 on screw 22 and internal threads 26 in abutment 20. When locking screw 22 is initially assembled into axial bore 44 of abutment 20, threads 30 will engage in threads 26 causing protrusion 32 to force open fingers 40 permitting it to pass therethrough. Flexible fingers 40 will snap in behind protrusion 32 locking the screw 22 into abutment 20. Additional advancement of threads 30 relative to internal threads 36 will cause conical taper 48 on locking screw 22 to engage the complementary sloping surfaces on the ends 41 of fingers 40. Operating in compression, locking screw 22 exerts a downwardly and outwardly directed force on said fingers 40 ensuring firm engagement with the hemispherical surface 18 formed on the top of fixture 12.

Figure 5:
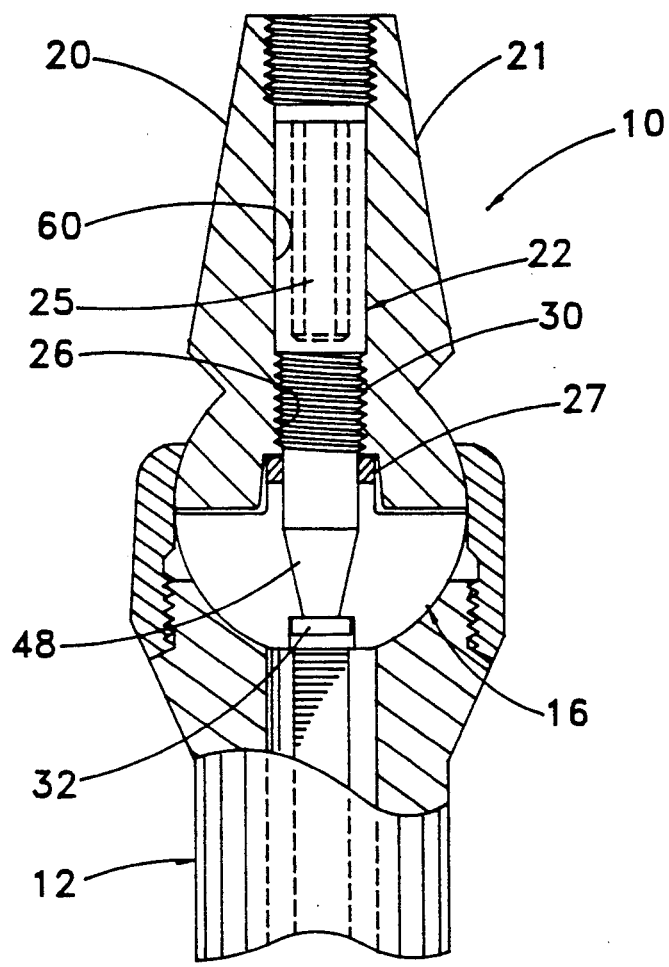
FIG. 5 is a cross-sectional side view of a fourth embodiment similar to that of FIG. 4 with a separate locking mechanism.

FIG. 5 depicts a fourth embodiment of dental prosthetic implant 10. Device 10 in this embodiment is similar to that of the third embodiment, except that the locking element 16 is formed as a separate hemisphere for ease of manufacture. Protrusion 32 on locking screw 22 performs a secondary function of retaining element 16 together with main body 21. The internal periphery of annulus 17 on the upper portion of locking element 16 may be threaded to permit engagement with threads 30. As the lower region of element are disengaged by protrusion 32, threads 30 will seat in threaded annulus 17. Inwardly tapered conical portion 48 will perform its expansion of fingers 40 in the same manner as the previous embodiment.

Figure 6:
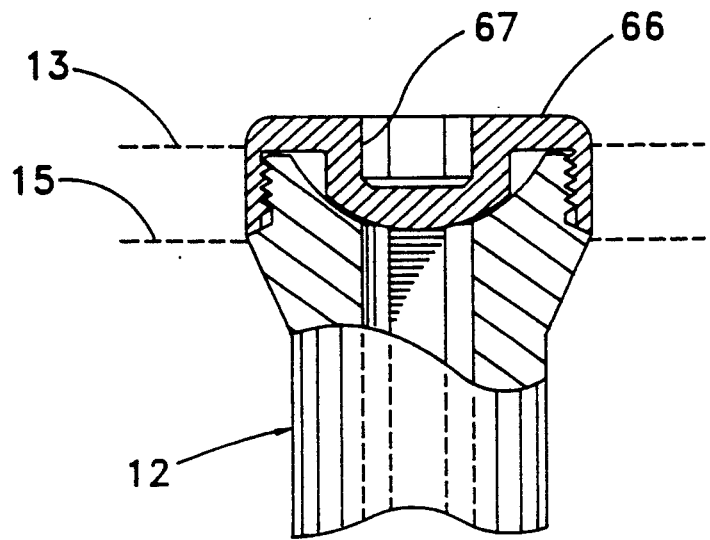
FIG. 6 is an enlarged cross-sectional side view of an implant fixture shown with a healing cap attached.

FIG. 6 depicts the implant fixture 12 with a healing cap 66 threaded on the upper end thereof using hex socket 67. After the fixture 12 is fastened into maxilla or mandible 15, the cap 66 is secured to its upper periphery and the soft tissue 13 is restored to the position shown in FIG. 6. Alternatively, soft tissue 13 may be sown over the top of healing cap 66. This will require a subsequent incision to provide access to the fixture 12 to permit the connection of the abutment 20 following the typically four to six month period required for the bone to integrate and captivate the threads of the fixture 12.

Figure 7:
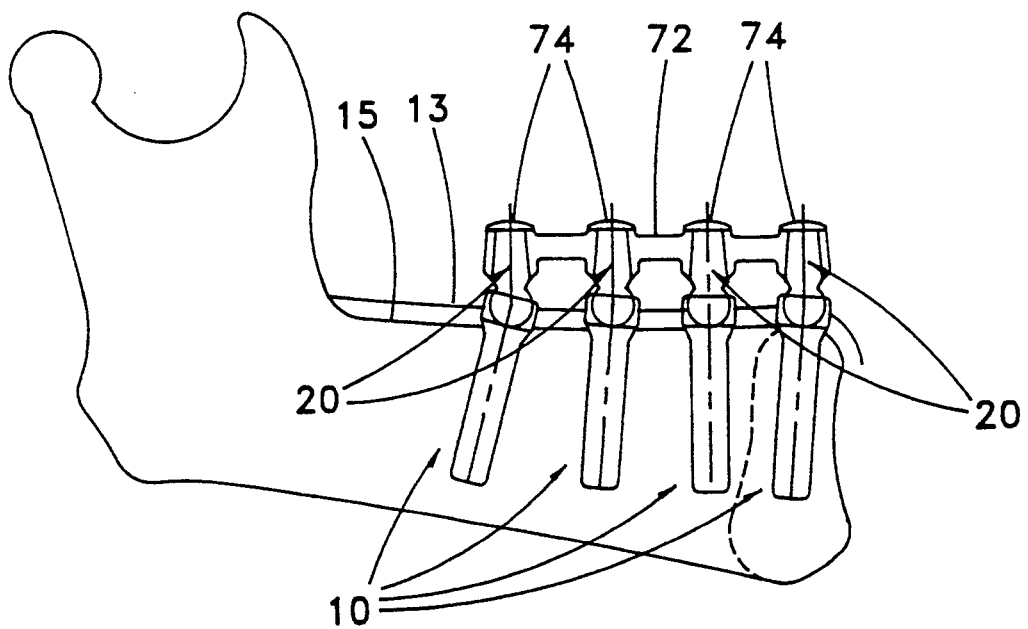
FIG. 7 is a schematic side view of a plurality of dental implants supporting a bar superstructure as might be located in a patient's mandible.

FIG. 7 depicts a plurality of implants 10 positioned at a variety of angles securing in place a support bar 72 with fixation screws 74. Screws 27 are threaded into the internal threads 26 of abutments 20 as previously discussed with respect to FIG. 1. The relative positions of the soft tissue 13 and mandible 15 can be seen. In use, support bar 72 is cast in situ of precious metal over sleeve 29 which is itself replaced by metal in a lost wax process. Support bar 72 receives a clip on dental bridge (not shown).

Figure 9:
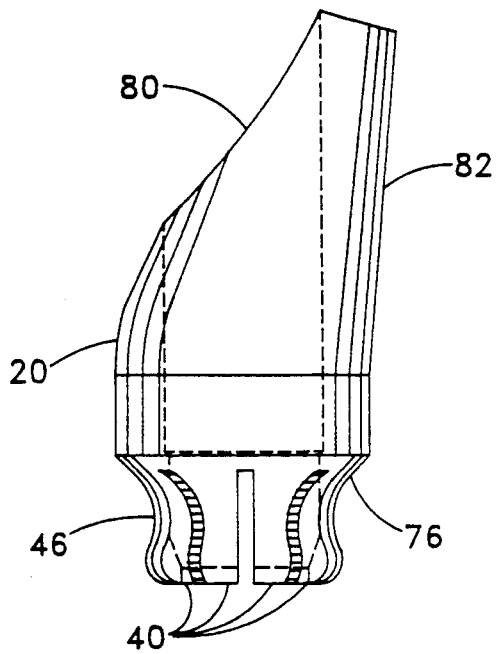
FIG. 9 is a side view of the dental implant fixture shown in FIG. 8.
Figure 8:
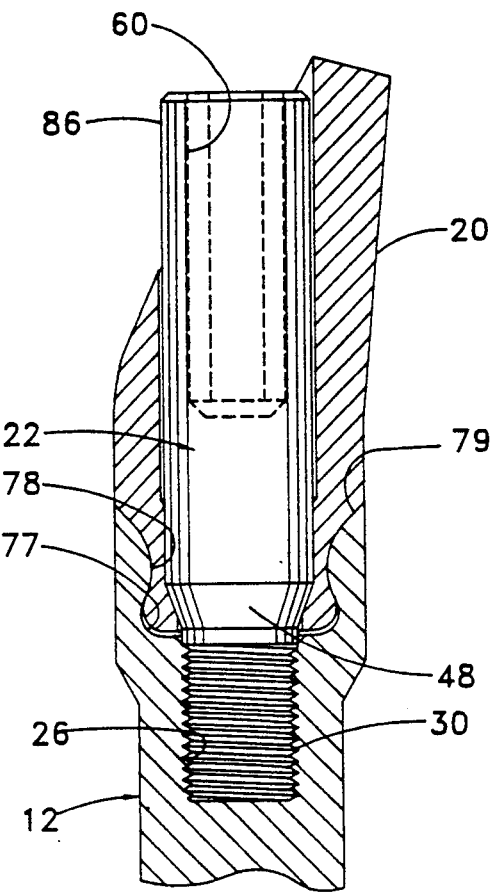
FIG. 8 is a side view in partial section of yet a fifth embodiment of the dental prosthesis of the present invention.
Figure 9A:
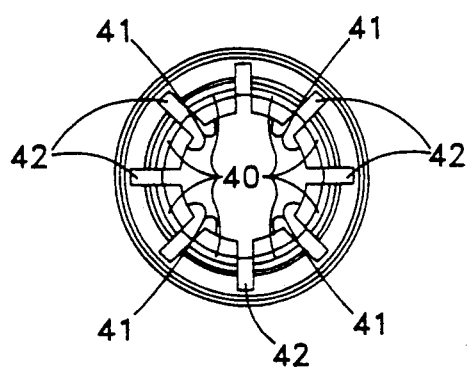
FIG. 9A is a bottom view of the dental implant fixture shown in FIG. 9.

A fifth embodiment of dental prosthetic implant 10 is depicted in FIGS. 8, 9 and 9A. In this embodiment, fixture 12 is formed with an undercut 77 below the minimum diameter 78. The top surface is 79 is formed with an angle preferably on the order of 45° for proper seating. Abutment 20 is generally conical with an angulated top surface 80 and lateral face 82, which define a conic generally equivalent to that found on earlier embodiments. The angularity of top surface 80 and lateral face 82 will vary generally in 5° increments.

Flexible fingers 40 are formed on the lower end of abutment 20 by an axial bore 44 which is intersected by diametrical slots 42. Minimum diameter 46 performs a function similar to that of groove 46 in earlier embodiments by providing a minimum dimension of the flexible fingers 40. Upper surface 76 has a complementarily angled surface to that of top surface 79 upon which it is to be seated. Ends 41 of fingers 40 have an inward taper which engage the similarly configured taper 48 an locking screw 22. Locking screw 22 is threaded at 30, which threads are received into threads 26 in the aperture in fixture 12. Hex socket 60 permits the locking screw 22 to be properly seated forcing flexible fingers 40 into engagement with fixture 12 preventing withdrawal and rotation, once proper rotational adjustment about the longitudinal axis has been made. The professional performing the installation procedure will then remove the the upper corner 86 of the locking screw 22 to make it conform to the angle of top surface 80. This type of implant is preferred for single tooth replacement, while the embodiments employing a spherical locking element are preferred for multiple tooth replacement requiring more complicated angular alignment and adjustment, particularly where a support bar 72 is used.

Figure 10:
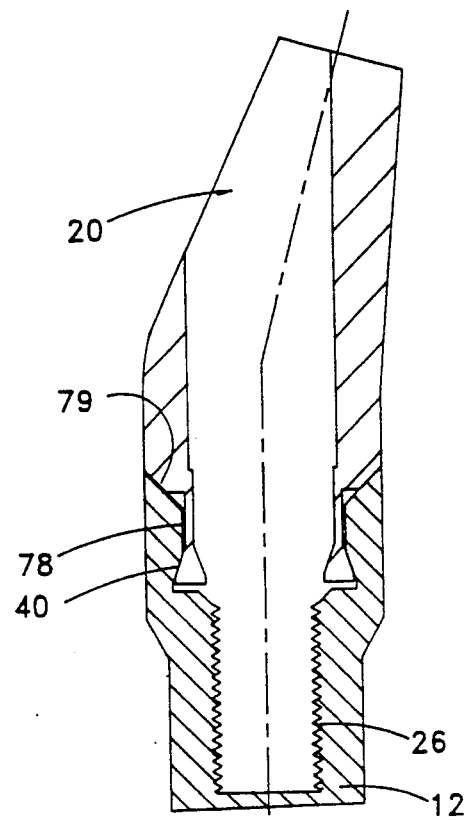
FIG. 10 is a side view of a sixth embodiment similar to the embodiment of FIG. 8.

FIG. 10 depicts a sixth embodiment of implant 10 similar to the previous embodiment. While the smooth curves shown in FIG. 8 are preferred for ease of manufacture and ease of installation, obviously the more angular configuration depicted here could also be used.

Various changes, alternatives, and modifications to the specific embodiments discussed above will become apparent to one of ordinary skill in the art following a reading of the foregoing specification. For example, the locking element could be formed as a separable, upper portion of the fixture, rather than as the lowermost element of the abutment. It is intended that all such changes, alternatives, and modifications as come within the scope of the appended claims be considered part of the present invention.

We claim:

1. A dental prosthetic implant comprising:
   a) an implant fixture receivable in a portion of a maxilla or mandible;
   b) an abutment attached to said implant fixture which forms at least a portion of a prosthetic tooth element;
   c) means for connecting said abutment to said implant fixture, said means including
      i) means for prohibiting relative axial and translational displacement, and
      ii) means for permitting relative rotational displacement for allowing adjustment to a particular desired rotational position;
   d) means for locking said abutment in said particular desired rotational position against further rotational displacement relative to said implant fixture, said means for locking including
      i) a first receiving surface associated with one of said implant fixture and said abutment, said first receiving surface having a minimum internal dimension.
      ii) a plurality of flexible fingers associated with another of said implant fixture and said abutment, said plurality of fingers having a maximum external dimension.
      iii) means for biasing said flexible fingers into engagement with said receiving surface with sufficient force to inhibit said relative rotational movement.
   whereby said means for biasing said flexible fingers increases said maximum external dimension of said fingers to a value greater than said minimum internal dimension of said receiving surface creating a mechanical interlock between said implant and said abutment.

2. The dental prosthetic implant of claim 1 wherein said means for permitting relative rotational displacement comprises a pair of complementary surfaces formed on said implant fixture and on said abutment, respectively.

3. The dental prosthetic implant of claim 2 wherein a first of said pair of complementary surfaces comprises said first receiving surface which is formed on said implant fixture.

4. The dental prosthetic implant of claim 3 wherein a second of said pair of complementary surfaces comprises an outer surface portion of said flexible fingers formed on said abutment.

5. The dental prosthetic implant of claim 4 further comprising a relief slot extending about a peripheral portion of said abutment to enhance flexibility of said flexible fingers.

6. The dental prosthetic implant of claim 5 wherein said relief slot is angulated upwardly as it proceeds inwardly for hygenic purposes to provide a flexing knuckle portion on said flexible fingers while keeping an outward exposed portion of said relief slot bounded by said abutment to avoid micromigration.

7. The dental prosthetic implant of claim 1 further comprising a hexagonally shaped central opening in said implant fixture for permitting rotational torque to be imparted to said fixture during implanting in said maxilla or mandible.

8. The dental prosthetic implant of claim 7 further comprising a healing cap extending over said central opening during a time immediately following said implanting.

9. The dental prosthetic implant of claim 1 wherein said abutment further comprises a laterally extending platform for seating a dental crown.

10. A dental prosthetic implant comprising:

a) an implant fixture receivable in a portion of a maxilla or mandible;
b) an abutment attached to said implant fixture which forms at least a portion of a prosthetic tooth element;
c) means for connecting said abutment to said implant fixture, said means including
   i) means for prohibiting relative axial and translational displacement, and
   ii) means for permitting relative rotational displacement for allowing adjustment to a particular desired rotational position including a pair of complementary surfaces formed on said implant fixture and on said abutment, respectively;
d) means for locking said abutment in said particular desired rotational position against further rotational displacement relative to said implant fixture, said means for locking including a pair of complementary surfaces including
   i) a first receiving surface associated with one of said implant fixture and said abutment,
   ii) a second surface including outer surface portions of a plurality of flexible fingers associated with another of said implant fixture and said abutment,
   iii) means for biasing said flexible fingers into engagement with said receiving surface with sufficient force to inhibit said relative rotational movement, said means for biasing including
       i) a first tapered surface on an inner surface portion of said flexible fingers;
       ii) a generally cylindrical locking screw having a second complementary tapered surface on a lower exterior region thereof for engaging said first tapered surface;
       iii) a threaded portion of said cylindrical locking screw positioned adjacent said second tapered surface, said threaded portion engaging a complementary internally threaded portion of said dental implant and providing means for exerting an outwardly directed force on said flexible fingers by means of said complementary tapered surfaces.

11. The dental prosthetic implant of claim 10 wherein said first tapered surface comprises an inwardly tapered surface and said locking screw is in compression, said threaded portion exerting a downwardly and outwardly directed force by means of said second tapered surface.

12. The dental prosthetic implant of claim 10 wherein said first tapered surface comprises an outwardly tapered surface and said locking screw is in tension, said threaded portion exerting an upwardly and outwardly directed force by means of said second tapered surface.

13. A dental prosthetic implant comprising:
a) an implant fixture receivable in a portion of a maxilla or mandible;
b) an abutment attached to said implant fixture which forms at least a portion of a prosthetic tooth element;
c) means for connecting said abutment to said implant fixture, said means including
   i) means for prohibiting relative axial and translational displacement, and
   ii) means for permitting relative rotational displacement for allowing adjustment to a particular desired rotational position including a pair of complementary surfaces formed on said implant fixture and on said abutment, respectively;
d) means for locking said abutment in said particular desired rotational position against further rotational displacement relative to said implant fixture, said means for locking including a pair of complementary surfaces including
   i) a first receiving surface associated with one of said implant fixture and said abutment,
   ii) a second surface including outer surface portions of a plurality of flexible fingers associated with another of said implant fixture and said abutment,
   iii) a relief slot extending about a peripheral portion of said abutment to enhance flexibility of said flexible fingers,
   iv) means for biasing said flexible fingers into engagement with said receiving surface with sufficient force to inhibit said relative rotational movement.

14. The dental prosthetic implant of claim 13 wherein said relief slot is angulated upwardly as it proceeds inwardly for hygenic purposes to provide a flexing knuckle portion on said flexible fingers while keeping an outward exposed portion of said relief slot bounded by said abutment to avoid microleakage.

15. A dental prosthetic implant comprising:
a) an implant fixture receivable in a portion of a maxilla or mandible;
b) an abutment attached to said implant fixture which forms at least a portion of a prosthetic tooth element;
c) means for connecting said abutment to said implant fixture, said means including
   i) a generally spherical ball formed upon one of said abutment and said fixture and a partially spherical recess for receiving said spherical ball on another of said abutment and said fixture, said flexible fingers being formed by an axial bore through said partially spherical ball and a plurality of diametrically extending slots cut in a lower hemisphere of said ball, whereby each of a series of planes defined by said plurality of slots contains a central axis of said axial bore
   ii) means for prohibiting relative axial and translational displacement, and
   iii) means for permitting relative rotational displacement for allowing adjustment to a particular desired rotational position;
d) means for locking said abutment in said particular desired rotational position against further rotational displacement relative to said implant fixture, said means for locking including
   i) a first receiving surface associated with one of said implant fixture and said abutment,
   ii) said plurality of flexible fingers associated with another of said implant fixture and said abutment,
   iii) means for biasing said flexible fingers into engagement with said receiving surface with sufficient force to inhibit said relative rotational movement.

16. The dental prosthetic implant of claim 15 wherein said plurality of diametrically extending slots comprise at least three equally angularly spaced slots defining at least six flexible fingers.

17. The dental prosthetic implant of claim 16 wherein said plurality of diametrically extending slots comprise at least four equally angularly spaced slots defining at least eight flexible fingers.

18. The dental prosthetic implant of claim 15 wherein said means for preventing relative axial and lateral displacement comprises a top seat threadingly engaged with a portion of an upper region of said implant fixture, said top seat encircling and captivating said generally spherical ball.

* * * * *